(12) United States Patent
Chiu et al.

(10) Patent No.: US 10,436,580 B2
(45) Date of Patent: Oct. 8, 2019

(54) SURFACE MEASUREMENT SYSTEM

(71) Applicant: CHROMA ATE INC., Tao-Yuan (TW)

(72) Inventors: Yi-Chang Chiu, Tao-Yuan (TW);
Cheng-Ting Tsai, Tao-Yuan (TW);
Shih-Yao Pan, Tao-Yuan (TW);
Lan-Sheng Yang, Tao-Yuan (TW);
Hsiu-Wei Kuo, Tao-Yuan (TW);
Shao-En Chung, Tao-Yuan (TW)

(73) Assignee: CHROMA ATE INC., Tao-Yuan (TW)

( * ) Notice: Subject to any disclaimer, the term of this patent is extended or adjusted under 35 U.S.C. 154(b) by 0 days.

(21) Appl. No.: 16/190,112

(22) Filed: Nov. 13, 2018

(65) Prior Publication Data
US 2019/0145762 A1    May 16, 2019

(30) Foreign Application Priority Data
Nov. 16, 2017 (TW) .............................. 106139765 A

(51) Int. Cl.
*G01B 11/30* (2006.01)
*G01N 21/51* (2006.01)
(Continued)

(52) U.S. Cl.
CPC ........... *G01B 11/303* (2013.01); *G01N 21/51* (2013.01); *G01N 21/958* (2013.01); *G01N 2021/4735* (2013.01)

(58) Field of Classification Search
CPC ..... G01N 2201/0612; G01N 2201/062; G01N 2201/12; G01N 21/3577; G01N 21/359; G01N 21/4795; G01N 21/49; G01N 2201/067; G01N 2201/129; G01N 33/4833; G01N 33/49; G01N 21/3504; G01N 21/76; G01N 33/54366; G01N 2021/6484;
(Continued)

(56) References Cited

U.S. PATENT DOCUMENTS 5,393,980 A * 2/1995 Yost ....................... G01N 21/33
                                                          250/305
5,444,529 A * 8/1995 Tateiwa ................. G01N 21/94
                                                          356/337
(Continued)

FOREIGN PATENT DOCUMENTS

| JP | 05-240797 A | 9/1993 |
| JP | 09-127006 A | 5/1997 |
| TW | I553304 B | 10/2016 |

*Primary Examiner* — Michael P Stafira
(74) *Attorney, Agent, or Firm* — CKC & Partners Co., LLC

(57) ABSTRACT

A surface measurement system is configured to measure a sample with a low reflectivity surface. The surface measurement system includes a condensation device and a measurement device. The condensation device is configured to form a liquid layer on the surface of the sample. The condensation device includes a chamber, a temperature controlling gas source, and a humidification gas source. The chamber is configured to accommodate the sample. The temperature controlling gas source is connected to the chamber to provide temperature controlling gases to the chamber, so as to control the temperature of the sample. The humidification gas source is connected to the chamber to provide water vapor to the chamber, so as to form the liquid layer on the surface of the sample. The measurement device includes a plate, a light source, and an image capturing device.

6 Claims, 5 Drawing Sheets

(51) Int. Cl.
*G01N 21/958* (2006.01)
*G01N 21/47* (2006.01)

(58) Field of Classification Search
CPC .... G01N 21/05; G01N 21/3563; G01N 21/59;
G01N 21/64; G01N 21/6428; G01N
21/645; G01N 21/78; G01N 2201/02;
G01N 2201/0621; G01N 2201/0697;
G01N 2201/08; G01N 2333/96433; G01N
33/54313; G01N 33/57434; G01N
35/1002; G01N 15/1404; G01N 15/1459;
G01N 15/1463; G01N 15/1475; G01N
15/1484; G01N 2015/1006; G01N
2021/3531; G01N 2021/3595; G01N
2021/4735; G01N 2021/6417; G01N
2021/6439; G01N 2021/6463; G01N
2021/6482; G01N 2021/8466; G01N
2035/00158; G01N 2035/00237; G01N
2035/00356; G01N 2035/0403; G01N
2035/042; G01N 2035/0425; G01N
2035/0494; G01N 2035/103; G01N
2035/1034; G01N 21/03; G01N 21/11;
G01N 21/253; G01N 21/27; G01N 21/51;
G01N 21/6452; G01N 21/6454; G01N
21/66; G01N 21/783; G01N 21/81; G01N
21/87; G01N 21/958; G01N 2201/023;
G01N 2201/025; G01N 2201/068; G01N
2201/0846; G01N 2201/0853; G01N
2333/01; G01N 33/004; G01N 33/0044;
G01N 33/0098; G01N 33/227; G01N
33/4925; G01N 33/497; G01N 35/00069;
G01N 35/00722; G01N 35/0098; G01N
35/02; G01N 35/026; G01N 35/028;
G01N 35/10; G01N 35/1065; G01N
35/1083; G02B 1/043; G02B 13/0085;
G02B 13/16; G02B 1/14; G02B
2027/0196; G02B 27/0093; G02B
27/0172; G02B 5/20; G02B 6/005; G01B
11/303; G01J 2003/1247; G01J
2003/2826; G01J 2003/2869; G01J
2005/0077; G01J 2005/604; G01J 3/0208;
G01J 3/021; G01J 3/0286; G01J 3/2803;
G01J 3/2823; G01J 3/32; G01J 3/36;
G01J 3/42; G01J 5/0014; G01J 5/0806;
G01J 5/0809; G01J 5/0896; G01J 5/522;
G01J 5/602

See application file for complete search history.

(56) References Cited

U.S. PATENT DOCUMENTS

| | | | |
|---|---|---|---|
| 7,598,037 B2 | 10/2009 | Perov et al. | |
| 2003/0147061 A1* | 8/2003 | Omura | G02B 13/143 355/67 |
| 2018/0188162 A1* | 7/2018 | Tanaka | G01N 21/3504 |

* cited by examiner

SURFACE MEASUREMENT SYSTEM

CROSS-REFERENCE TO RELATED APPLICATION

This application claims priority to Taiwan Application Serial Number 106139765, filed Nov. 16, 2017, which is herein incorporated by reference in its entirety.

BACKGROUND

Field of Invention

The present disclosure relates to a surface measurement system.

Description of Related Art

With the development of technology, transparent materials (e.g., glass) are used in more and more electronic products for product components (e.g., mobile phone panels, cell phone shells, or lenses). In order to ensure quality, the transparent components can be measured to get their surface topography. However, the transparent material has a problem of low reflectivity. To get images with sufficient accuracy, it is necessary to increase the exposure time and/or light source intensity in measuring. If there are flaws at the inner or bottom of the component, they may also be measured and cause signal misjudgment. In addition, if the surface of the component is curved, multiple reflections may also occur.

SUMMARY

One aspect of the present disclosure provides a surface measurement system for measuring a sample having a surface with low reflectivity. The surface measurement system includes a condensation device and a measurement device. The condensation device is configured to form a liquid layer on the surface of the sample. The condensation device includes a chamber, a temperature controlling gas source, and a humidification gas source. The chamber is configured to accommodate the sample. The temperature controlling gas source is connected to the chamber and configured to provide temperature controlling gases to the chamber, so as to control the temperature of the sample. The humidification gas source is connected to the chamber and configured to provide water vapor to the chamber, so as to form the liquid layer on the surface of the sample. The measurement device includes a plate, a light source, and an image capturing device. The plate is configured to place the sample having the liquid layer. The light source is configured to provide a light beam to illuminate the sample on the plate. The image capturing device is configured to detect the light beam scattered from the sample on the plate.

Another aspect of the present disclosure provides a surface measurement system for measuring a sample having a surface with low reflectivity. The surface measurement system includes a temperature controlling device, a humidification device, and a measurement device. The temperature control device includes a temperature controlling chamber and a temperature controlling gas source. The temperature controlling chamber is configured to accommodate the sample. The temperature controlling chamber is connected to the temperature controlling chamber and configured to provide temperature controlling gas, so as to control the temperature of the sample. The humidification device includes a humidification chamber and a humidification gas source. The humidification chamber is configured to accommodate the temperature-controlled sample. The humidification gas resource is connected to the humidification chamber to provide water vapor to the humidification chamber, so as a liquid layer is formed on the surface of the sample. The measurement device includes a plate, a light source, and an image capturing device. The plate is configured to place the sample having the liquid layer. The light source is configured to provide a light beam to illuminate the sample on the plate. The image capturing device is configured to detect the light beam scattered from the sample on the plate.

According to the surface measurement systems of the above-mentioned embodiments, a liquid layer is formed on the surface of the sample to increase the scattering amount of the light beam illuminating the surface. As a result, the acquired images have high signal-to-noise ratios, such that the surface can be measured accurately, and the measurement speed can also be increased.

It is to be understood that both the foregoing general description and the following detailed description are by examples, and are intended to provide further explanation of the invention as claimed.

BRIEF DESCRIPTION OF THE DRAWINGS

The present disclosure can be more fully understood by reading the following detailed description of the embodiment, with reference made to the accompanying drawings as follows.

DETAILED DESCRIPTION

The following discloses several embodiments of the present disclosure. For clarity, many practical details will be illustrated in the following description. However, it should be understood that these practical details should not be limiting. In other words, in some embodiments of the present disclosure, the practical details are not essential. In addition, in order to simplify the figures, some conventionally known structures and elements are schematically illustrated in the figures.

Figure 1:
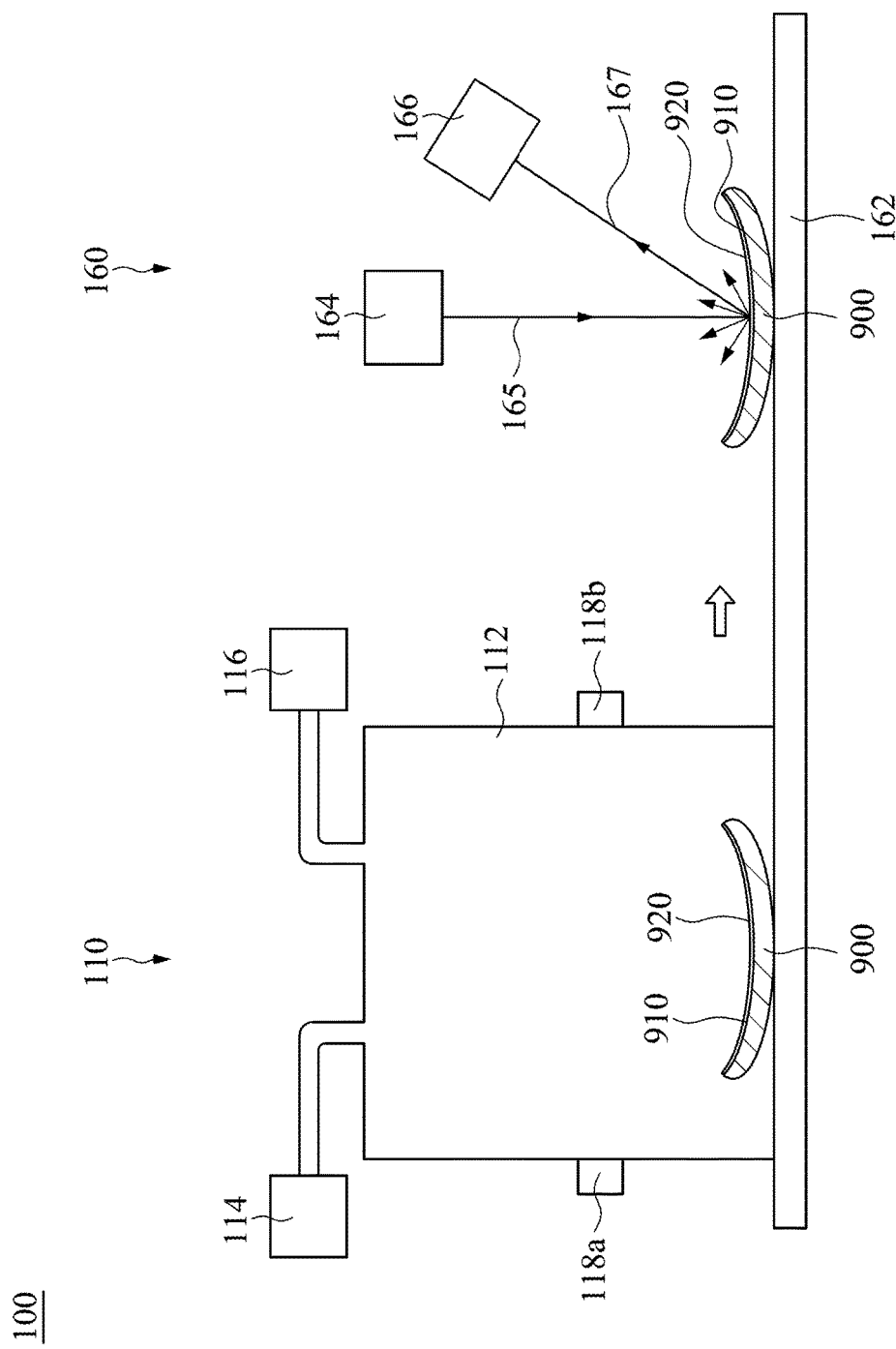
FIG. 1 is a schematic diagram of the surface measurement system, according to one embodiment of the present disclosure.

FIG. 1 is a schematic diagram of the surface measurement system 100 according to an embodiment of the present disclosure. The surface measurement system 100 is configured to measure the sample 900 having the surface 910 with low reflectivity. The surface measurement system 100 includes a condensation device 110 and a measurement device 160. The condensation device 110 is configured to form a liquid layer 920 on the surface 910 of the sample 900. The measurement device 160 is configured to measure the sample 900 having the liquid layer 920.

Specifically, in this embodiment, the condensation device 110 is used to form a liquid layer 920 on the surface 910 having low reflectivity; therefore, when the measurement device 160 illuminates the surface 910, the light scatters on the liquid layer 920, so as to increase the amount of light received by the measurement device 160, and reduce the increasing noise signals from the multiple reflections of the sample 900.

In detail, the sample 900 in this embodiment may be transparent or translucent materials, such as glass, plastic, or other suitable materials. The surface 910 of the sample 900 has low reflectivity; therefore, when the light illuminates the surface 910 (the upper surface of the sample 900 in this embodiment), most of the light penetrates the sample 900. As a result, the amount of the reflective light captured by the measurement device 160 is relatively few, evenly too few to image, resulting in the difficulties in the surface measurement. Further, the lower surface of the sample 900 also reflects some light, which interferes with the reflected light from the upper surface and generates noise signals, resulting in more difficulties in image identification. In addition, if the surface 910 of the sample 900 is a curved surface (as shown in FIG. 1), the reflected directions of light on the various sites of the surface 910 are different, resulting in more difficulties in image capturing.

However, in the present embodiment, a liquid layer 920 is formed on the surface 910 before the measurement of the surface 910, the liquid layer 920 can increase the amount of light scattering, such that the above-mentioned problems of insufficient reflectivity and inconsistent reflected directions can be improved. In addition, the liquid layer 920 can also block the light reflected from the lower surface, so as to lower the image noise signals and improve the quality of image capturing.

Figure 2B:
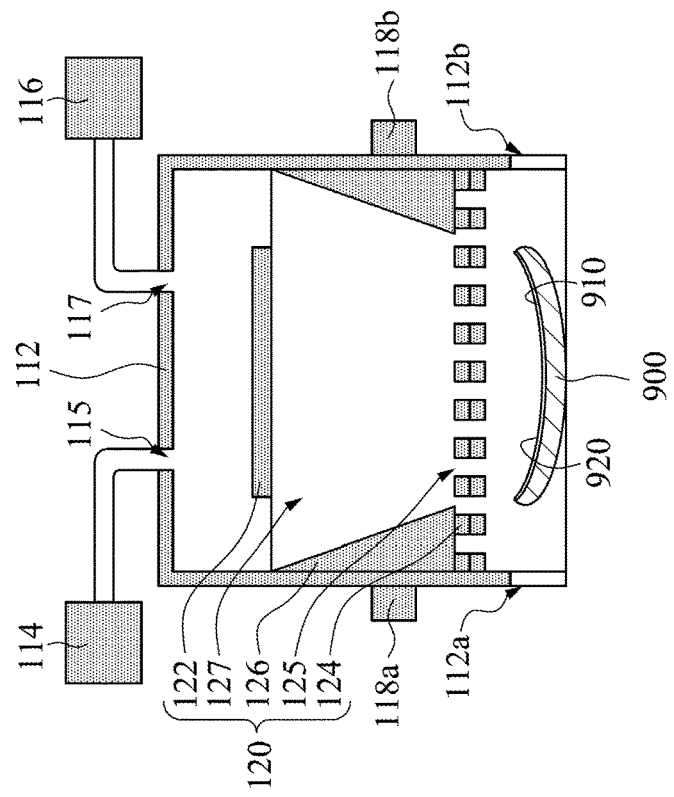
FIG. 2B is a cross-sectional view of the condensation device and the sample of FIG. 1.
Figure 2A:
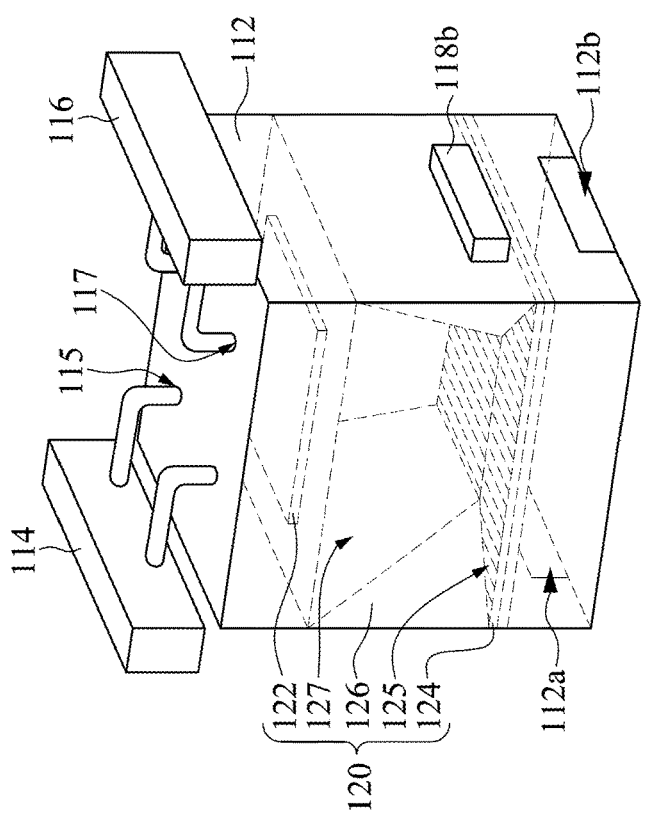
FIG. 2A is a perspective view of the condensation device of FIG. 1.

FIG. 2A is a perspective view of the condensation device 110 of FIG. 1, and FIG. 2B is a cross-sectional view of the condensation device 110 and the sample 900 of FIG. 1. The condensation device 110 includes a chamber 112, a temperature controlling gas source 114, and a humidification gas source 116. The chamber 112 is configured to accommodate the sample 900. The temperature controlling gas source 114 is connected to the chamber 112 and configured to provide temperature controlling gases to the chamber 112 to control the temperature of the sample 900. The humidification gas source 116 is connected to the chamber 112 and configured to provide water vapor to the chamber 112 to form a liquid layer 920 on the surface 910 of the sample 900.

Specifically, the sample 900 for surface measurement is placed in the chamber 112, then the temperature controlling gas source 114 provides the temperature controlling gas (e.g. Air or other suitable gases) to the chamber 112. The temperature of the temperature controlling gas is different from the temperature of the chamber 112, for example, the temperature of the temperature controlling gas is lower than the temperature (e.g., room temperature) of the chamber 112; therefore, when the temperature controlling gas enters the chamber 112, the temperature of the sample 900 can be changed (e.g., cooling the sample 900) by air convection.

Next, the humidification gas source 116 provides water vapor to the chamber 112. Because the temperatures of the chamber 112 and the sample 900 have been lowered, the water vapor provided to the chamber 112 is more likely to saturate and condense into a liquid, and a liquid layer 920 (its composition is liquid water) is formed on the surface 910 of the sample 900 by condensation. Then, the sample 900 with the liquid layer 920 can leave the condensation device 110 and be transferred to the measurement device 160 of FIG. 1 for surface measurement.

Although in the above-mentioned embodiment, the liquid layer 920 is formed by cooling and then humidifying; in some other embodiments, the water vapor may be provided to the chamber 112 to increase the humidity of the chamber 112, and then the temperature controlling gas may be provided to lower the temperature of the sample 900; or the temperature controlling gas and the water vapor may be supplied together; the liquid layer 920 can be formed by all of the above-mentioned steps. In addition, because the air temperature in the chamber 112 is lowered in the above-mentioned embodiment, it is not necessary for the chamber 112 to be in a high humidity environment for condensation, thus rust and mold can be avoided.

The uniform liquid layer 920 can increase the scattering effect; in this disclosure, uniform means that the liquid droplets (e.g., water droplets) of the liquid layer 920 have similar dimensions, for example, the diameters of the liquid droplets are about 2 micrometers to about 5 micrometers, and/or there are similar spacings between the liquid droplets. The uniformity of the liquid layer 920 relates to the formation temperature (determined by the temperature controlling gas) and the flow field of the gas in the chamber 112. Therefore, in some embodiments, the condensation device 110 may further include a diversion structure 120 disposed in the chamber 112. The diversion structure 120 is configured to control the flow field of the temperature controlling gas and the water vapor, and uniformly guide the temperature controlling gas and the water vapor to the sample 900 to form a uniform liquid layer 920 on the sample 900.

In FIG. 2A and FIG. 2B, the diversion structure 120 includes a diffusion plate 122 and a rectifier plate 124. The diffusion plate 122 is disposed in front of the gas outlet 115, and between the rectifier plate 124 and the temperature controlling gas source 114. The gas outlet 115 is the exit for the temperature controlling gas exiting from the temperature controlling gas source into the chamber 112. The rectifier plate 124 has a plurality of through holes 125 configured to uniformize the flow directions of the temperature controlling gas. Specifically, the diffusion plate 122 may be a flat plate; when the temperature controlling gas enters the chamber 112 through the gas outlet 115, the temperature controlling gas will contact the diffusion plate 122 and then be reflected by the diffusion plate 122, thereby the route of the temperature controlling gas change, resulting in the irregular flow directions of the temperature controlling gas, hence the temperature controlling gas can uniformly flow in the chamber 112. The temperature controlling gas then reaches the rectifier plate 124 which only permits the passing of a temperature controlling gas in the specific angle/direction, and this angle/direction depends on the setting of the through holes 125. The through holes 125, for example, are disposed vertically (as shown in FIG. 2B), so only the temperature controlling gas in vertical direction can pass through. In addition, the temperature controlling gas in a large angular direction hits the inner walls of the through holes 125 and is reflected. After multiple reflections, the route directions of the temperature controlling gas are directed to a substantially vertical direction. As a result, the temperature controlling gas passing through the rectifier plate 124 is collimated, that is, the flow directions are uniformized. The temperature controlling gas with uniformized flow directions can uniformly lower the temperature of the sample 900 to avoid uneven temperature drop.

In addition, the diffusion plate 122 can further be disposed in front of the gas outlet 117 of the humidification sources 116, and between the rectifier plate 124 and the humidification gas source 116. The gas outlet 117 here is the exit for the water vapor exiting from the humidification gas source 116 into the chamber 112. The rectifier plate 124 is also configured to uniformize the flow directions of the water vapor. As described above, when the water vapor of the humidification gas source 116 enters the chamber 112, the water vapor will contact the diffusion plate 122 and then be reflected by the diffusion plate 112, so that the water vapor can uniformly flow in the chamber 112. The rectifier plate 124 also can collimate the flow directions of the water vapor to uniformize the flow directions of the water vapor. The water vapor with uniformized directions can uniformly condense on the surface 910 of the sample 900 to achieve the liquid layer 920 with uniform liquid droplet dimensions and/or spacings. In some embodiments, the Reynolds number of the flow field of the water vapor with uniformized directions is about 10 to about 100; however, this is not intended to be limiting.

It is noted, the position and the number of the gas outlets 115 and 117 of FIG. 2A and FIG. 2B are merely examples and are not intended to be limiting. Persons having ordinary skill in this field should optionally select the position and number of the gas outlets 115 and 117 according to actual needs. In addition, as long as the diffusion plate 122 is disposed in front of at least one of gas outlets 115 and 117, such case is within the scope of the present invention.

In some embodiments, the diversion structure 120 may further include an air collecting plate 126, which is disposed between the diffusion plate 122 and the rectifier plate 124 and configured to concentrate the temperature controlling gas and the water vapor. Specifically, the temperature controlling gas and the water vapor passing through the diffusion plate 122 have non-uniform flow directions, so some of the temperature controlling gas and the water vapor may not reach the rectifier plate 124, and the air collecting plate 126 can concentrate the temperature controlling gas and the water vapor to increase the amount of the temperature controlling gas and the water vapor reaching the rectifier plate 124. In some embodiments, the air collecting plate 126 has a channel 127, and the width of the channel 127 tapers along the direction from the diffusion plate 122 to the rectifier plate 124, so that the temperature controlling gas and the water vapor in a large angle can be concentrated. In some embodiments, the air collecting plate 126 may have a triangular cross-section (as shown in FIG. 2B), and the channel 127 may have an inverted trapezoidal cross-section, but these are not intended to be limiting. In addition, in FIG. 2A and FIG. 2B, the inner surface of the channel 127 is planar; however, in other embodiments, the inner surface may be curved to increase the efficiency of collecting/concentrating the temperature controlling gas and the water vapor.

In FIG. 2A and FIG. 2B, the chamber 112 has an inlet 112a and an outlet 112b. The sample 900 can enter the chamber 112 through the inlet 112a, and leave the chamber 112 through the outlet 112b. In some embodiments, the inlet 112a and the outlet 112b may be open, that is, the chamber 112 may not have a valve for opening or closing the inlet 112a and the outlet 112b. The condensation device 110 may further include air door devices 118a and 118b, which are respectively disposed on the inlet 112a and the outlet 112b. The air door devices 118a and 118b have vents configured to produce high-pressure airflow, which can isolate the air inside the chamber 112 from the air outside the chamber 112 to achieve an effect of close. However, in other embodiments, for the inlet 112a and the outlet 112b, other ways or structures may be used to isolate the air inside the chamber 112 from the air outside the chamber 112, and these are not intended to be limiting.

Referring back to FIG. 1 The measurement device 160 includes a plate 162, a light source 164, and an image capturing device 166. The plate 162 is configured to place the sample 900 having the liquid layer 920. The light source 164 is configured to provide a light beam 165 to illuminate the sample 900 on the plate 162. The image capturing device 166 is configured to detect the beam 167 scattered from the sample 900 on the plate 162. Specifically, when the liquid layer 920 is formed on the sample 900 in the condensation device 110, the sample 900 leaves the condensation device 110 from the outlet 112b (as shown in FIG. 2B) to the plate 162 of the measurement device 160. In some embodiments, the sample 900 can be moved by means of a conveyor belt or a manual way. In addition, the light source 164 may be a laser or other suitable light emitting elements; the image capturing device 166 may be a camera, but this is not intended to be limiting. Moreover, the measurement device 160 can measure the surface 910 of the sample 900 by using a laser triangulation method, a structured light measurement method, or other suitable measurement methods.

It is noted, in the following description, the details that have been mentioned in the above embodiments will not be described repeatedly, and only the differences in the following embodiments are described in detail.

Figure 3:
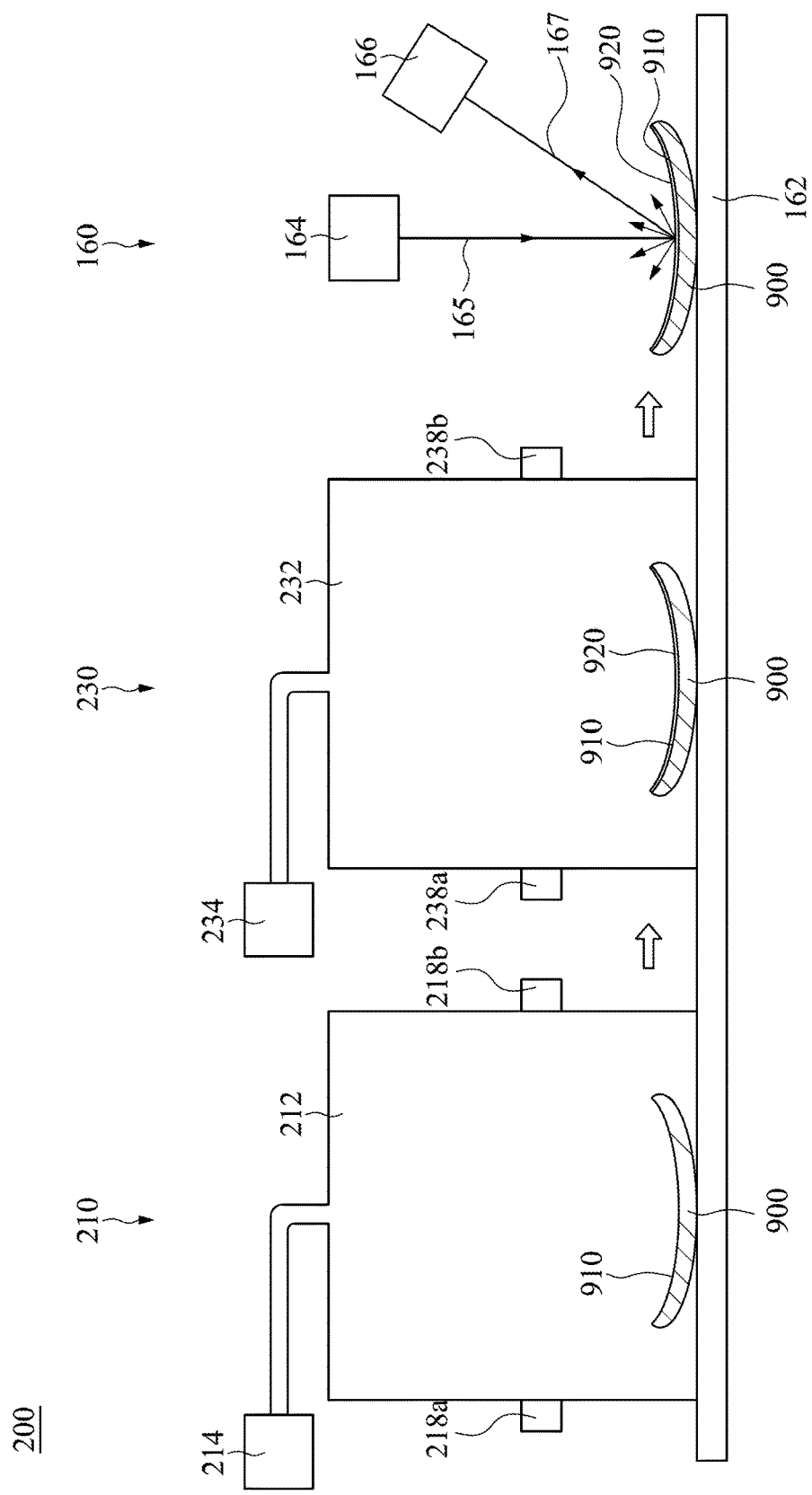
FIG. 3 is a schematic diagram of the surface measurement system, according to another embodiment of the present disclosure.

FIG. 3 is a schematic diagram of the surface measurement system 200 of another embodiment of the present disclosure. The surface measurement system 200 includes a temperature controlling device 210, a humidification device 230, and a measurement device 160. The temperature controlling device 210 is configured to control the temperature of the sample 900, and the humidification device 230 is configured to form a liquid layer 920 on the surface 910 of the sample 900. The measurement device 160 is configured to measure the sample 900 with the liquid layer 920.

Figure 4B:
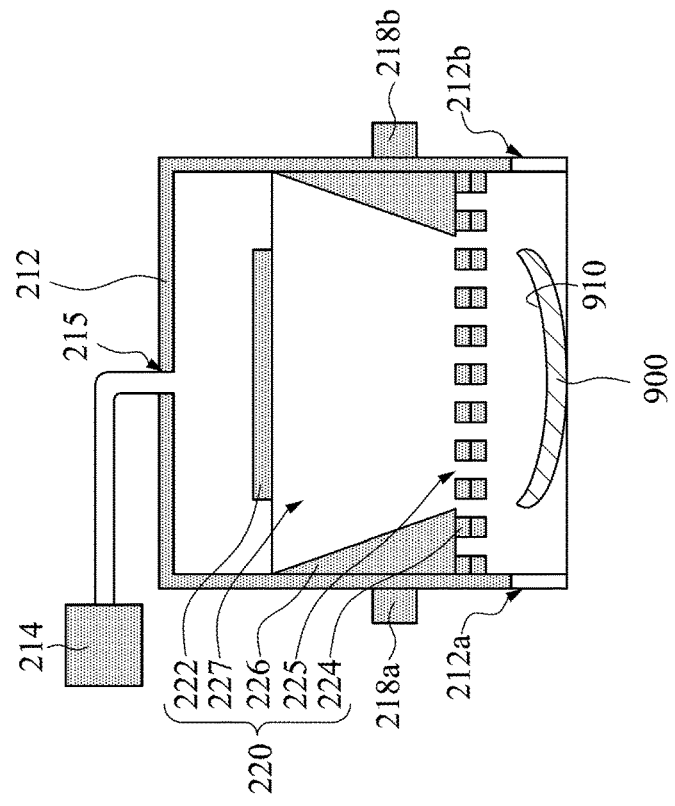
FIG. 4B is a cross-sectional view of the temperature controlling device and sample of FIG. 3.
Figure 4A:
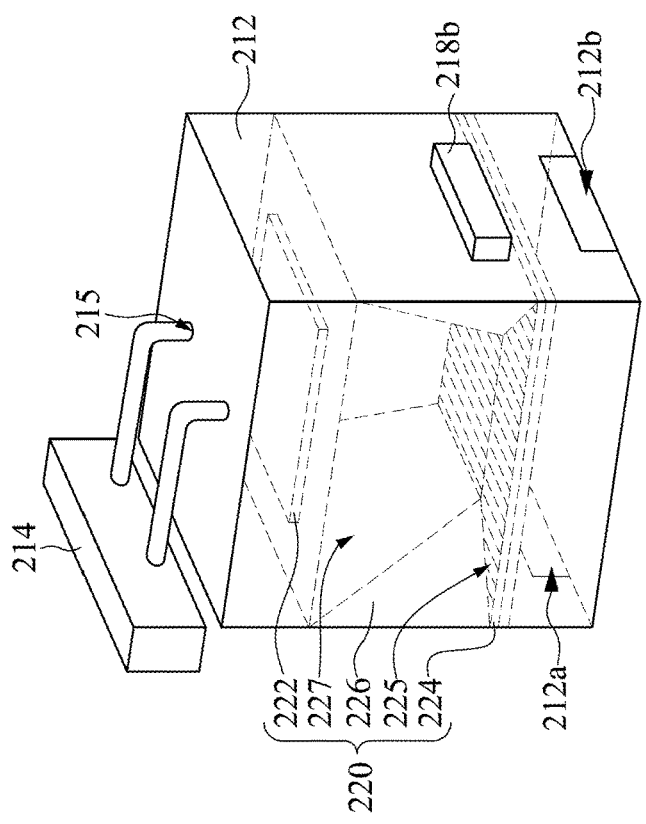
FIG. 4A is a perspective view of the temperature controlling device of FIG. 3.

FIG. 4A is a perspective view of the temperature controlling device 210 of FIG. 3, and FIG. 4B is a cross-sectional view of the temperature controlling 210 and the sample 900 of FIG. 3. The temperature controlling device 210 includes a temperature controlling chamber 212 and a temperature controlling gas source 214. The temperature controlling chamber 212 is configured to accommodate the sample 900. The temperature controlling gas source 214 is connected to the temperature controlling chamber 212 and configured to provide the temperature controlling gas to the temperature controlling chamber 212 to control the temperature of the sample 900. Specifically, the sample 900 for surface measurement is placed in the temperature controlling chamber 212, then the temperature controlling gas source 214 provides the temperature controlling gas to the temperature controlling chamber 212 to change the temperature of sample 900, for example, cooling the sample 900.

In some embodiments, the temperature controlling device 210 may further include a diversion structure 220, which is disposed in the chamber 212. The diversion structure 220 is configured to control the flow field of the temperature controlling gas, and uniformly guide the temperature controlling gas to the sample 900, so as to achieve the purpose of uniform cooling the sample 900. The diversion structure 220 includes a diffusion plate 222 and a rectifier plate 224. The diffusion plate 222 is disposed in front of the gas outlet 215 of the temperature controlling gas source 214, and between the rectifier plate 224 and the temperature controlling gas source 214. The rectifier plate 224 has a plurality of through holes 225 configured to uniformize the flow directions of the temperature controlling gas. As a result, the temperature controlling gas passing through the rectifier plate 224 is collimated, that is, the flow directions are uniformized. The temperature controlling gas with the uniformized flow directions can uniformly lower the temperature of the sample 900 to avoid uneven temperature drop.

In some embodiments, the diversion structure 220 may further include a gas collecting plate 226, which is disposed between the diffusion plate 222 and the rectifier plate 224 and configured to concentrate the temperature controlling gas. In some embodiments, the gas collecting plate 226 has a channel 227, and the width of the channel 227 tapers along the direction from the diffusion plate 222 to the rectifier plate 224, so that the temperature controlling gas in a large angle can be concentrated.

In addition, the temperature controlling chamber 212 has an inlet 212a and an outlet 212b. The sample 900 can enter the temperature controlling chamber 212 through the inlet 212a, and leave the temperature controlling chamber 212 through the outlet 212b. The temperature controlling device 210 can further include air door devices 218a and 218b, which are respectively disposed on the inlet 212a and the outlet 212b. The air door devices 218a and 218b have vents configured to produce high-pressure airflow, which can isolate the air inside the temperature controlling chamber 212 from the air outside the temperature controlling chamber 212 to achieve an effect of close. As other details of the temperature control device 210 in this embodiment are similar to the condensation device 110 of FIG. 2A and FIG. 2B, they will not be repeatedly described.

Figure 5B:
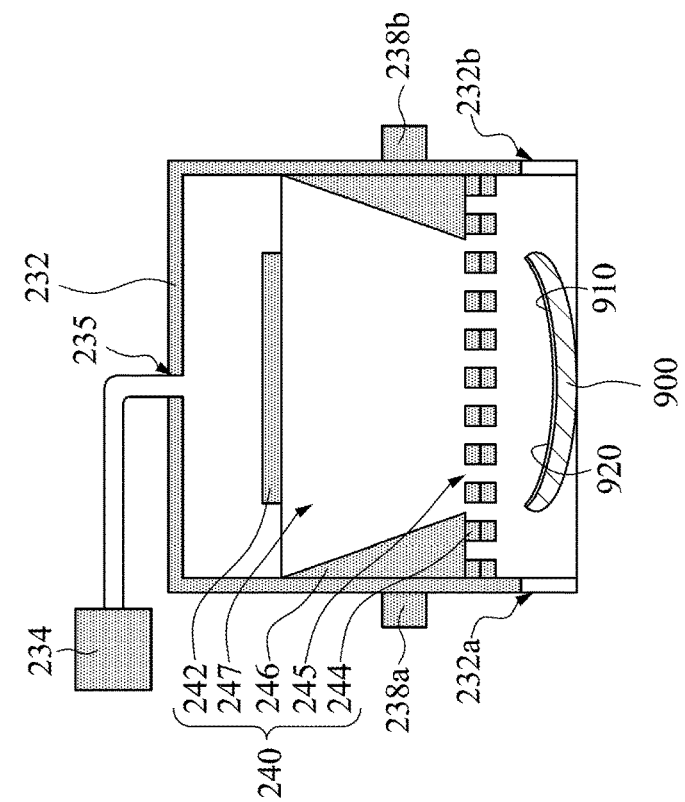
FIG. 5B is a cross-sectional view of the humidification device and the sample of FIG. 3.
Figure 5A:
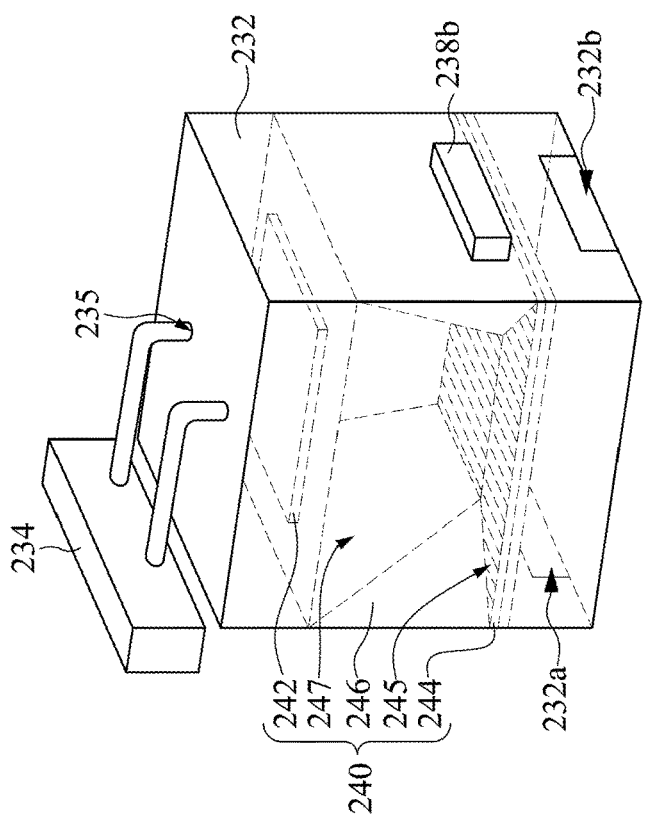
FIG. 5A is a perspective view of the humidification device of FIG. 3.

FIG. 5A is a perspective view of the humidification device 230 of FIG. 3; FIG. 5B is a cross-sectional view of the humidification device 230 and the sample 900 of FIG. 3. The humidification device 230 includes a humidification chamber 232 and a humidification gas source 234. The humidification chamber 232 is configured to accommodate the temperature-controlled the sample 900 (i.e., the sample 900 leaving the temperature controlling device 210 of FIG. 3). The humidification gas source 234 is connected to the humidification chamber 232 and configured to provide water vapor to the humidification chamber 232 to form a liquid layer 920 on the surface 910 of the sample 900. Specifically, the humidification gas source 234 provides water vapor to the humidification chamber 232. Because the temperature of the sample 900 is lowered, the water vapor is more likely to saturate and condense into liquid on the surface 910 of the sample 900, and then form a liquid layer 920 whose composition is liquid water. After that, the sample 900 with liquid layer 920 formed can exit from the humidification device 230 and be moved to the measurement device 160 of FIG. 3 for surface measurement.

In some embodiments, the humidification device 230 may further include a diversion structure 240, which is disposed in the humidification chamber 232. The diversion structure 240 is configured to control the flow field of the water vapor and evenly guide the water vapor to the sample 900 to form a uniform liquid layer 920 on the sample 900. The diversion structure 240 includes a diffusion plate 242 and a rectifier 244. The diffusion plate 242 is disposed in front of the air outlet 235 of the humidification gas source 234, and between the rectifier plate 244 and the humidification gas source 234. The rectifier plate 244 has a plurality of through holes 245 configured to uniformize the flow direction of the water vapor. As a result, the water vapor passing through the rectifier plate 244 is collimated, that is, the flow directions are uniformized. The water vapor with uniformized directions can uniformly condense on the surface of the sample 900 to form a uniform liquid layer 920.

In some embodiments, the diversion structure 240 may further include air collecting plate 246, which is disposed between the diffusion plate 242 and the rectifier plate 244 and configured to concentrate water vapor. In some embodiments, the air collecting plate 246 has a channel 247, the width of the channel 247 tapers along the direction from the diffusion plate 242 to the rectifier plate 244, so that the water vapor in large angle can be concentrated.

In addition, the humidification chamber 232 has an inlet 232a and an outlet 232b. The sample 900 may enter the humidification chamber 232 through the inlet 232a, and leave the humidification chamber 232 through the outlet 232b. The humidification device 230 may further include air door devices 238a and 238b disposed respectively on the inlet 232a and the outlet 2323b. The air door devices 238a and 238b have air outlets configured to produce high-pressure airflow, which can isolate the air inside the humidification chamber 232 from the air outside the humidification chamber 232 to achieve an effect of close. As other details of the humidifying device 230 in this embodiment are similar to that of the condensation device 110 of FIG. 2A and FIG. 2B, they will not be repeatedly described. In addition, after the liquid layer 920 is formed, the sample 900 leaves the humidification device 230, and the surface measurement is carried out on the measurement device 160. As the elements and the measuring methods of the measurement device 160 in this embodiment are similar to those of the measurement device 160 of FIG. 1, they will not be repeatedly described.

To sum up, for the surface measurement system in the above-mentioned embodiments, a liquid layer is formed on the surface of the sample to increase the scattering amount of the light beam illuminating the surface. As a result, the measured images have high signal-to-noise ratios, so that the surface can be accurately measured and the measurement speed can also be increased.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A surface measurement system for measuring a sample having a surface with low reflectivity, the surface measurement system comprising:
    a condensation device configured to form a liquid layer on the surface of the sample, the condensation device comprising:
        a chamber configured to accommodate the sample;
        a temperature controlling gas source connected to the chamber and configured to provide a temperature controlling gas to the chamber to control temperature of the sample;
        a humidification gas source connected to the chamber and configured to provide water vapor to the chamber to form the liquid layer on the surface of the sample; and a diversion structure disposed in the chamber and configured to uniformly guide the temperature controlling gas and the water vapor to the sample, wherein the diversion structure comprises:
  a diffusion plate disposed in front of a gas outlet of the temperature controlling gas source; and
  a rectifier plate, wherein the diffusion plate is disposed between the rectifier plate and the temperature controlling gas source, the rectifier plate has a plurality of through holes configured to uniformize flow directions of the temperature controlling gas and the water vapor; and
a measurement device comprising:
  a plate configured to place the sample with the liquid layer;
  a light source configured to provide a light beam to illuminate the sample on the plate; and
  an image capturing device configured to detect the light beam scattered from the sample on the plate.

2. The surface measurement system of claim 1, wherein the diversion structure further comprises:
  a gas collecting plate disposed between the diffusion plate and the rectifier plate and configured to concentrate the temperature controlling gas and the water vapor.

3. The surface measurement system of claim 2, wherein the gas collecting plate has a channel, and a width of the channel gradually tapers along a direction from the diffusion plate to the rectifier plate.

4. A surface measurement system for measuring a sample having a surface with low reflectivity, the surface measurement system comprising:
  a temperature controlling device, comprising:
    a temperature controlling chamber configured to accommodate the sample;
    a temperature controlling gas source connected to the temperature controlling chamber and configured to provide a temperature controlling gas to the temperature controlling chamber to control temperature of the sample; and
    a diversion structure disposed in the temperature controlling chamber, the diversion structure is configured to uniformly guide the temperature controlling gas to the sample, wherein the diversion structure comprises:
      a diffusion plate disposed in front of an air outlet of the temperature controlling gas source; and
      a rectifier plate, wherein the diffusion plate is disposed between the rectifier plate and the temperature controlling gas source, the rectifier plate having a plurality of through holes configured to uniformize flow directions of the temperature controlling gas;
  a humidification device, comprising:
    a humidification chamber configured to accommodate the sample at a controlled temperature; and
    a humidification gas resource connected to the humidification chamber and configured to provide water vapor to the humidification chamber to form a liquid layer on the surface of the sample; and
  a measurement device, comprising:
    a plate configured to place the sample having the liquid layer;
    a light source configured to provide a light beam to illuminate the sample on the plate; and
    an image capturing device configured to detect the light beam scattered from the sample on the plate.

5. The surface measurement system of claim 4, wherein the diversion structure further comprises:
  a gas collecting plate disposed between the diffusion plate and the rectifier plate and configured to concentrate the temperature controlling gas.

6. The surface measurement system of claim 5, wherein the gas collecting plate has a channel, and a width of the channel gradually tapers along a direction from the diffusion plate to the rectifier plate.

* * * * *